Figure 1A:
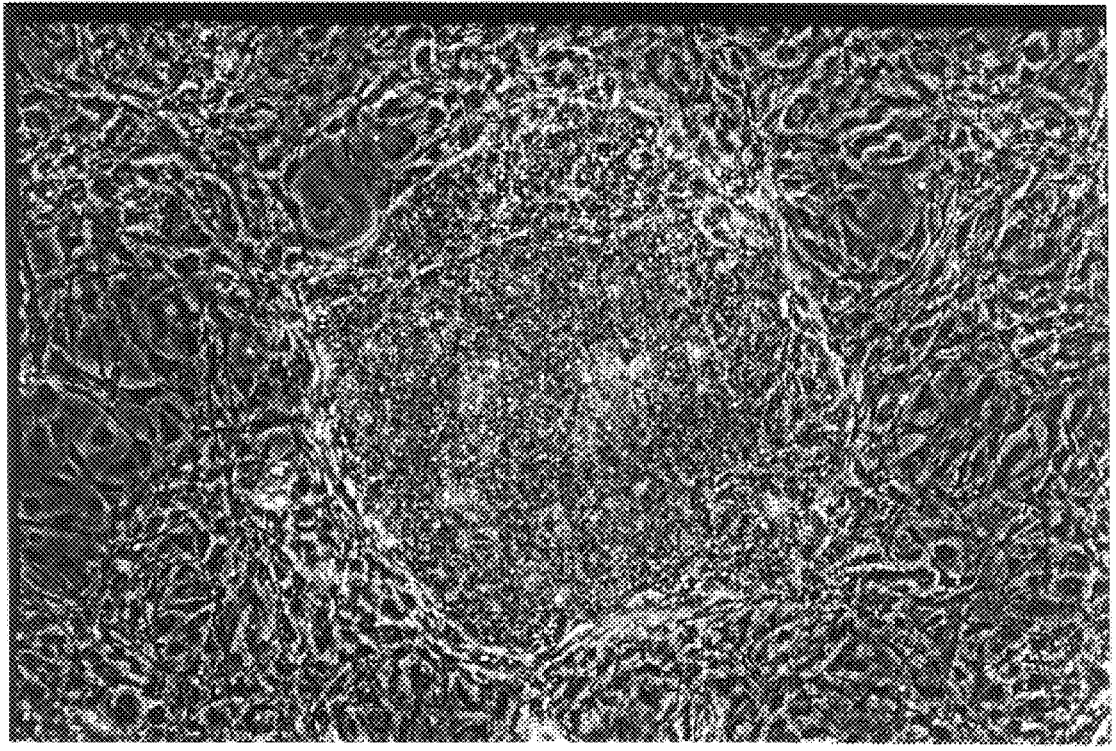

United States Patent [19]
Moreadith et al.

[11] Patent Number: 6,103,523
[45] Date of Patent: Aug. 15, 2000

[54] PLURIPOTENT RABBIT CELL LINES AND METHOD OF MAKING

[75] Inventors: Randall Moreadith, Chapel Hill, N.C.; Luc Schoonjans, Wilsele, Belgium

[73] Assignee: Thromb-X N.V., Leuven, Belgium

[21] Appl. No.: 08/810,945

[22] Filed: Feb. 27, 1997

[30]     Foreign Application Priority Data

Apr. 29, 1996 [EP] European Pat. Off. .............. 96201169
Nov. 4, 1996 [EP] European Pat. Off. .............. 96203060

[51] Int. Cl.$^7$ .............................. C12N 5/00; C12N 5/02; C12N 9/66
[52] U.S. Cl. ......................... 435/325; 435/213; 435/378; 435/405; 435/406; 435/408
[58] Field of Search ................................ 800/2; 435/325, 435/213, 378, 405, 406, 408

[56]           References Cited

PUBLICATIONS

Nichols et al (1990) Development 110, 1341–1348.
Bradley et al (1992) Biotechnology 10, 534–539.
Wurst et al in Gene Targeting: A Practical Approach, A. L. Joyner, ed., IRL Press, Oxford university Press, Oxford, England, 1993, pp. 33–61.
Clark et al in Transgenic Animals, F. Grosveld and G. Kollais, eds., Academic Press, London, England, 1992, pp. 247–270.
"Derivation and characterization of putative pluripotential embryonic stem cells from preimplantation rabbit embryos," Graves et al., Molecular Reproduction and Development, vol. 6, pp. 424–433.
"Pluripotency of cultured rabbit inner cell mass cells detected by isozyme analysis and eye pigmentation of fetuses following injection into blastocysts or Morulae,".
Giles et al., Molecular Reproduction and Development, vol. 36, pp. 130–138 (1993).
"Nuclear transfer of putative rabbit emvryonic stem cells leads to normal blastocyst development," Du et al., Journal of Reproduction and Fertility, vol. 104. pp. 219–223 (1995).
"A method for cultivating morphologicalcy undifferentiated embryonic stem cells from porcine blastocytes," Strojek et al., Theriogenology, vol. 33, No. 4, pp. 901–913 (1990).
"Dispersing and Disruption of Tissue," Bashor, Methods in Enzymology, Academic Press, vol. LVIII, pp. 119–131 (1979).

*Primary Examiner*—Deborah Crouch
*Attorney, Agent, or Firm*—Webb Ziesenheim Logsdon Orkin & Hanson, P.C.

[57]           ABSTRACT

The present invention relates to a rabbit embryonic stem (ES) cell line, comprising at least 70%, preferably 80 to 90% undifferentiated cells and obtainable by isolating the inner cell mass of 5.5 days postcoitus blastocysts and culturing them on feeder cells in rabbit ES medium. The invention further relates to further optimization of derivation and maintainance of the cell line and to the use thereof in inter alia generation of chimeric rabbits.

3 Claims, 3 Drawing Sheets

PLURIPOTENT RABBIT CELL LINES AND METHOD OF MAKING

The present invention relates to novel rabbit embryonic stem (ES) cell lines and their use in the generation of chimeric rabbits.

Gene targeting (via homologous recombination in embryonic stem (ES) cells) technology allows the manipulation of the genome in desired and defined ways (Capecchi, 1989; Robertson, 1987; Bradley, 1987). Briefly, genes to be targeted are incorporated in plasmid transfer vectors and altered by replacement of some of their sequence with foreign DNA which encodes selectable markers (inactivation) or by a mutated gene sequence (targeted mutagenesis). These inactivated or mutated genes are then introduced into ES cells (which each have the potential to develop into a complete animal). Subsequently clones of ES cells in which the natural gene is replaced by the inactivated hybrid are selected in vitro, and these selected clones are introduced into normal embryos which are reimplanted. This process generates chimeric animals which are selected for germline transmission of the inactivated gene. Through breeding and selection, transgenic animals are then generated which are deficient in the targeted ("knocked-out") gene.

Completely ES cell derived mice can be generated utilising the recently developed technology to aggregate wild type or mutant ES cells with tetraploid embryos (Nagy et al., 1993). Alternatively ES cells can be used for introduction of genetic material by non-homologous recombination, allowing the study of genetic alteration in live animals.

The application of transgenic technologies and ES cell technologies for the alteration of gene function has provided animal models of important human diseases (for review cfr. Wilson, 1996; Rubin and Barsch, 1996). However, at present this technology has only been successful in the mouse. Although useful for many applications, the mouse has significant restrictions (e.g. size and inability to generate the phenotype of human diseases) that limit its potential applications. Consequently, larger animal models to test the phenotypic consequences or loss-of-function mutations would be very valuable.

Presumptive pluripotential ES cells have been isolated in a number of additional species including hamster (Doetschman et al., 1988), pig (Evans et al., 1990; Piedrahita et al., 1990; Notarianni et al., 1990; Talbot et al., 1993), sheep (Notarianni et al., 1990), cattle (Evans et al.; Saito et al., 1992), mink (Sukoyan et al., 1993), rabbit (Graves and Moreadith, 1993), rat (Iannaccione et al., 1994), man (Bongso et al., 1994) and primate (Thomson et al., 1995). However, only in the mouse and rat ES cells have been established in culture giving rise to chimeras following reintroduction into blastocysts, whereas all efforts in the rabbit and other species have failed to date.

Inner cell mass (ICM) cells freshly derived from rabbit blastocysts have been shown to allow the generation of chimeric rabbits following injection into recipient blastocysts (Gardner and Munro, 1974; Moustafa, 1974; Babinet and Bordenave, 1980), whereas Yang et al. (1993) have reported the production of chimeric rabbits both from freshly isolated ICM and from ICM cells maintained in culture in vitro for 3 days.

However, in order to allow gene targeting by homologous recombination in ES cells, cell lines that can be kept in culture for a longer period of time and with demonstrated potential to generate chimeric animals are necessary for the production of offspring with targeted genetic alterations.

Prior to the present invention, no such cell lines of animals other than mice and rats had been isolated.

Figure 1B:
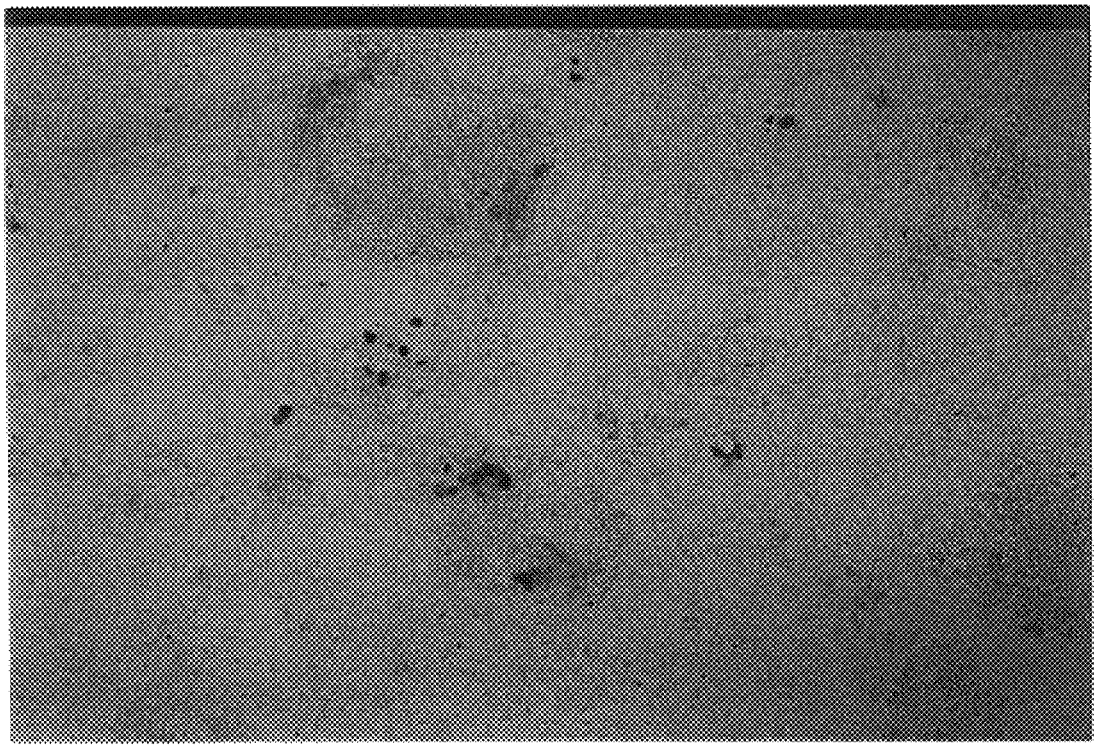

The derivation of putative pluripotential rabbit ES cells was previously reported by Graves and Moreadith (1993). Two principal cell types emerged following serial passage of explanted embryos. One type had morphology identical to primary outgrowths of trophectoderm, cells that are responsible for embryo implantation. The second type appeared typically epitheloid and was presumed to represent rabbit ES cells (FIG. 1). Although these putative ES cells were able to generate embryoid bodies, consisting of multiple cell types representative of ectoderm, mesoderm and endoderm, they were unable to produce chimeric rabbits after introduction of the epitheloid cells into blastocysts from the New Zealand White (NZW) strain (Graves and Moreadith, 1993; Graves and Moreadith, unpublished results (Table 1)) or after nuclear transfer into a denucleated New Zealand White zygote (Du et al., 1995). It was suggested that the inability to produce chimeras with these ES cells could have been due to a strain barrier. Nevertheless, the data in Table 1 demonstrate that no chimeric animals could be derived from any of the four tested epitheloid lines, each derived from a single inner cell mass.

TABLE 1

Results of rabbit embryo injection with putative ES cell lines (unpublished results, Graves and Moreadith)

| cell line | stage of embryo | #injections | #born (%) | chimeras (%) |
|---|---|---|---|---|
| GM3 | blastocyst | 46 | 29 (63) | 0 (0) |
| GM4 | blastocyst | 24 | 2 (8) | 0 (0) |
| GM8 | morula | 84 | 6 (7) | 0 (0) |
| GM4 | morula | 14 | 5 (35) | 0 (0) |
| Total | | 168 | 42 (25) | 0 (0) |

Niemann and Strelchenko (1994) also attempted to isolate and maintain pluripotent rabbit (California strain) ES cells but, although aggregation of the putative ES cells (maintained for a total of 12 passages) with the inner cell mass of the host blastocyst (Chinchilla, Black Rex) was observed, generation of chimeric offspring was not documented. These putative ES cells were derived from rabbit embryos collected 4 days after mating. Thus, to date, all efforts to generate stable pluripotent rabbit ES cell lines, with the demonstrated potential to generate chimeric animals following injection into recipient blastocysts, have failed.

It is therefore the object of the invention to come to the improved derivation and maintenance of rabbit embryonic stem (ES) cells with demonstrated potential to generate chimeric rabbits following injection in recipient blastocysts, thus enabling the production of wild type or genetically altered offspring (via either homologous or non-homologous recombination, using for example gene or nuclear transfer).

It was now found that a rabbit embryonic stem (ES) cell line, comprising at least 70%, preferably 80 to 90% undifferentiated cells is obtainable by isolating the inner cell mass of 5.5 days postcoitus blastocysts and culturing them on feeder cells in rabbit ES medium.

The rabbit ES medium according to the invention comprises high glucose Dulbecco's Modified Eagle Medium, 4 mM L-glutamine, 0.1 mM 2-mercaptoethanol, 148 units/ml penicillin G sodium, 148 microgram/ml streptomycin sulfate, 4 microgram/ml bovine insulin, $10^3$ units/ml murine Leukemia Inhibitory Factor, 20% fetal bovine serum, 1.5% MEM non-essential amino acid solution.

The feeder cells are preferably mouse embryonic fibroblasts derived from 12.5 days old mouse embryos and used in a density of 3 to $4\times10^6$ cells per 10 cm petri dish.

Preferably also a modified trypsinization method was used, which consists of the use of trypsinization medium comprising 0.1% collagenase, 1% chicken serum and 0.03% trypsin-EDTA in phosphate-buffered saline. This medium allowed the selective passage of ES cells because mouse embryonic fibroblasts and trophectodermal cells detach more slowly in this medium.

Cells according to the invention are recognisable by virtue of their following properties: three dimensional colony formation, positive staining for alkaline phosphatase and negative staining for cytokeratin 18 and vimentin after more than 10 passages.

The invention further relates to the use of the ES cell lines for the generation of chimeric rabbits, for example following blastocyst injection into recipient blastocysts or embryo aggregation or nuclear transfer.

The ES cell lines of the invention may also be used for gene alteration by homologous or non-homologous recombination or for the generation of rabbits with gene alteration via germline transmission.

The use or differentiation of cell lines according to the invention can lead to the study or isolation of (novel) genes.

The present invention thus leads to the improved derivation of pluripotent ES cells, their maintenance in culture over several passages, and their use for the successful generation of chimeric animals.

The derivation and maintenance of rabbit ES cells with demonstrated potential to generate chimeric rabbits following injection in recipient blastocysts will allow the generation of offspring capable of germline transmission of the targeted mutations following homologous or non-homologous recombination in these pluripotent ES cells. In addition, the pluripotency of the rabbit ES cells will allow to differentiate them into defined cell types enabling the study or isolation of novel genes.

LEGENDS TO THE FIGURES

FIGS. 1(A–B): Rabbit ES cells (GM3 line), derived by Graves and Moreadith. A) phase constrast microscopy of the putative ES cells revealing a flat epithleoid pehnotype; B) alkaline phosphatase staining of the putative ES cells, showing a very low percentage (<1 percent) of alkaline phosphatase positive cells (red).

Figure 2A:
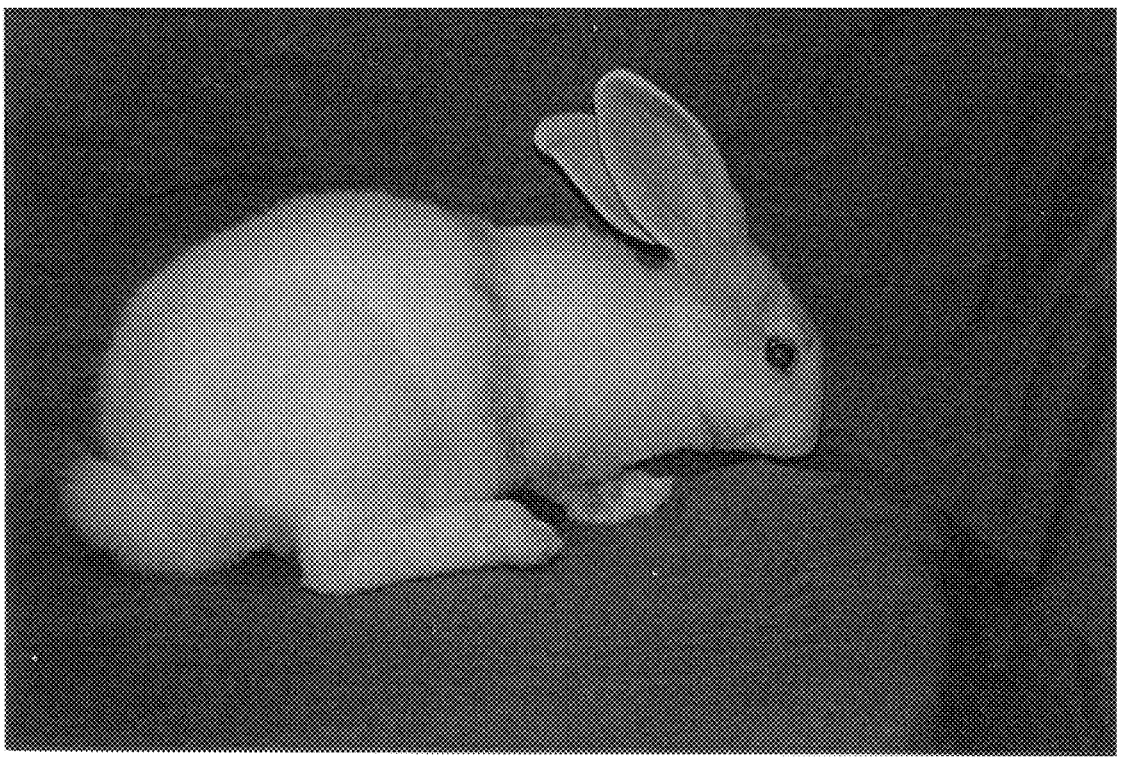
Figure 2B:
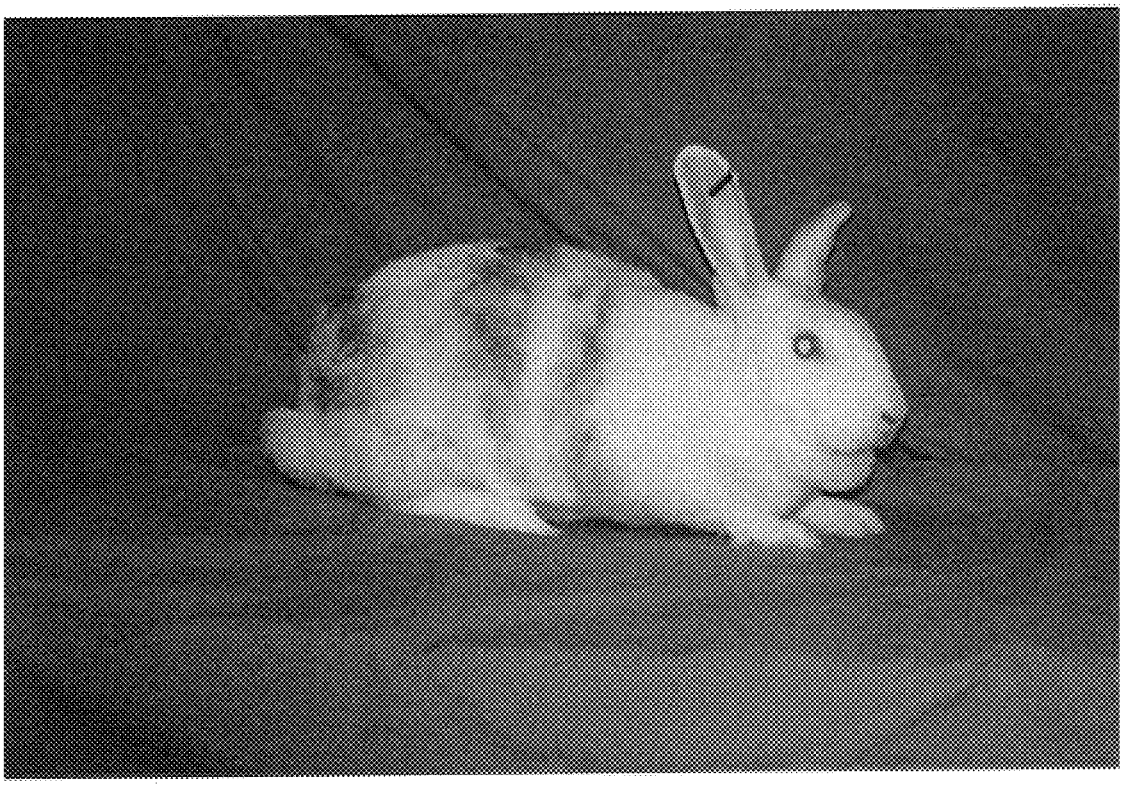

FIGS. 2(A–B): A) Male chimera with one black belt; B) female chimera showing several black belts. The belts are typical for the Dutch Belted strain from which the GM3 ES cell line was derived.

Figure 3A:
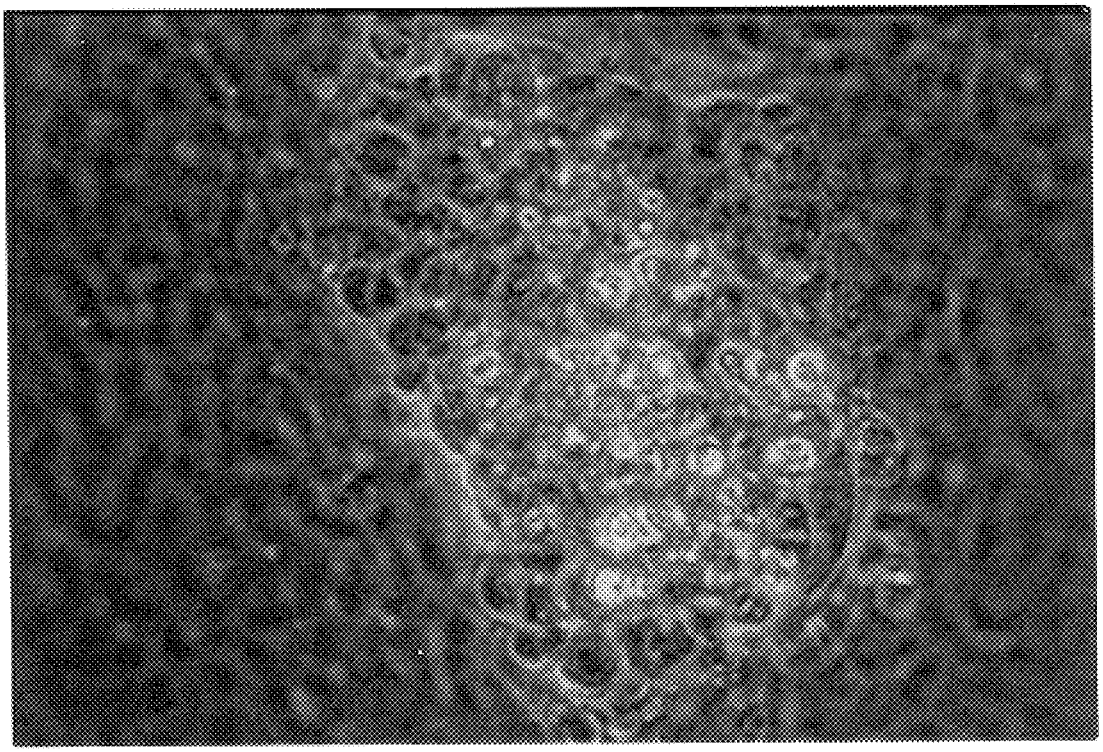
Figure 3B:
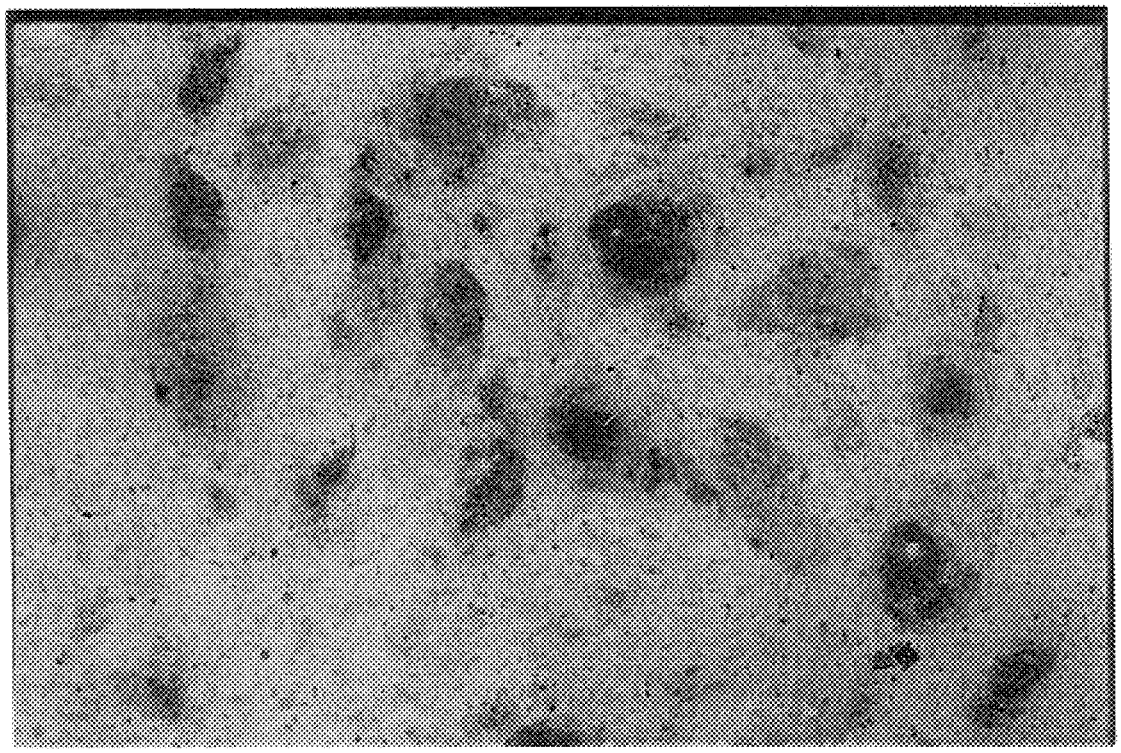

FIGS. 3(A–B): A) phase constrast microscopy of a newly derived cell line using the improved cell culture and ES derivation conditions described herein; B) alkaline phosphatase staining of a rabbit ES cell line derived using the improved cell culture and ES derivation condtions described herein. The new ES cell line is characterized by three dimensional growth, high refractibility and 80 to 90% alkaline phosphatase positive staining.

The invention will be illustrated in the following examples, that are not intended to limit the scope of the invention. Based on the present invention, several variants and improvements will be obvious to those skilled in the art.

EXAMPLE 1

Cell Culture Conditions

Starting from the ES cell line GM3, derived from Dutch Belted rabbit embryos as described by Graves and Moreadith (1993) (FIG. 1), cell culture conditions were developed which stabilized the percentage of undifferentiated ES cells, relative to the methods described by Graves and Moreadith (1993). Thus, it became possible, for the first time, to generate chimeras after injection of ES cells into the blastocoel cavity of New Zealand White blastocysts, as will be demonstrated in Example 2.

Changes were made to the cell culture medium, the density of the mouse embryonic fibroblast (MEF) feeder layers, the age of the mouse embryos used to derive the MEFs, and the trypsinization medium used to dislodge cells for passage.

The culture medium used by Graves and Moreadith (1993) consisted of high glucose Dulbecco's Modified Eagle Medium, 4 mM L-glutamine, 0.1 mM 2-mercaptoethanol, penicillin G sodium 148 U/ml, and streptomycin sulfate 148 μg/ml.

According to the invention the following supplements were changed or added: 4 μg/ml bovine insulin, $10^3$ units/ml of murine Leukemia Inhibitory Factor, 20% fetal bovine serum, 1.5% MEM non-essential amino acid solution.

The rabbit ES cells (1.5 to $3\times10^6$ cells per 10 cm petridish) were grown to subconfluency on mouse embryonic fibroblasts mitotically arrested with mitomycin and the ES cells were passaged every 4–6 days onto freshly prepared feeders (3 to $4\times10^6$ cells per 10 cm dish). The ES cells were fed every day with the improved medium described above. Culture dishes were kept at 39° C. in a humidified atmosphere of 5% $CO_2$ in air. The mouse embryonic fibroblast were derived from 12.5 day old mouse embryos and were used at passage 1. The increased density of the mouse embryonic fibroblasts (3 to $4\times10^6$ as compared to 2 to $3\times10^6$ cells per 10 cm dish (Graves and Moreadith, 1993)) together with the use of 12.5 days embryos markedly reduced the differentiation of the ES cells.

This reduction of differentiation proved to be crucial, since only undifferentiated cells maintain the capacity to incorporate in the inner cell mass of a recipient embryo, a prerequisite to give rise to chimeric offspring.

Furthermore, an improved selective trypsinization method was used which allowed the removal of trophectodermal cells (which can induce ES cell differentiation) from the culture. The trypsinization medium consisted of 0.1% collagenase, 1% chicken serum and 0.03% trypsin-EDTA (Gibco Cat. no. 25200) in phosphate buffered saline. This selective trypsinization medium allowed the selective passage of ES cells because mouse embryonic fibroblasts and trophectodermal cells detach more slowly from the culture dish than ES cells.

EXAMPLE 2

Generation of Chimeras

The GM3 cells, derived from Dutch Belted embryos by Graves and Moreadith (1993), but maintained in culture conditions in Example 1, were used to generate chimeric offspring as described below. Blastocyst injection of the epitheloid colonies of the putative ES cells had previously never generated chimeric rabbits after injection into rabbit embryos (Table 1). For further experiments described below, GM3 cells from passage 12 were maintained in improved culture conditions which stabilized the percentage of alkaline phosphatase positive, undifferentiated ES cells.

Sexually mature New Zealand White females were superovulated with six consecutive subcutaneous injections of porcine follicle stimulating hormone (FSH-0.4, 0.4, 0.5, 0.5, 0.5, 0.5 mg) given 12 hours apart, followed by 75 IU of human chorionic gonadoptropin (hCG) given intravenously 10 hours after the last dose of FSH. Following the hCG injection, the females were mated with mature males of the same strain.

Blastocysts were recovered from the uterine horns 90 hours after mating, by flushing the uterine cavity with Dulbecco's phosphate buffered saline supplemented with 3% bovine serum albumin (Cohn fraction V) plus 5% antibiotic/antimycotic solution (Gibco, Grand Island, N.Y.) which had been pre-equilibrated at 39° C. in a humidified atmosphere of 5% $CO_2$ in air.

Chimeras were generated by injection of both epitheloid alkaline phosphatase negative and the three dimensionally growing alkaline phosphatase positive ES cells into the blastocoel cavity of New Zealand White blastocyst (Table 2). A total of 287 New Zealand White blastocysts were injected with 20 to 300 cells from the GM3 cell line. Blastocyst injections with GM3 cells were performed on a Zeiss inverted microscope with differential interference optics at a magnification of 250×. Micromanipulations were performed with Narashige micromanipulators as routinely employed for the mouse.

Between 5 and 10 embryos injected with GM3 cells were reimplanted into the proximal portion of each uterine horn of a recipient New Zealand White doe using a small incision and a sharpened glass pipette. This recipient doe had previously received 75 IU of hCG, 14 hours after the time of hCG injection in the donors. The reimplantation procedure was done under general anesthesia with a ketamine/xylazine mixture.

TABLE 2

Production of chimeras after injection of ES cells into the blastocoel cavity of New Zealand White blastocysts

| #blasts | injected | #ES cells | passage | #born (%) | #chimeras (%) |
|---|---|---|---|---|---|
| | 76 | 20–30 | 22 | 30 (41) | 1 (1) |
| | 124 | 50–100 | 15 | 31 (25) | 1 (1) |
| | 87 | 100–300 | 18 | 6 (7) | 1 (1) |
| Total | 287 | | | 67 (23) | 3 (1) |

Percentages in parentheses are relative to numbers of blastocysts injected.

This procedure resulted in an overall live birth rate of 23%. Since the ES cell line used was derived from the pigmented Dutch Belted strain, injection of GM3 ES cells into blastocysts from a nonpigmented New Zealand White strain will generate overt coat color formation in chimeras. As judged by coat color, three chimeric animals were obtained with one or more black belts, typical for the Dutch Belted strain. The percentage of chimerism varied between 10% to more than 50%, based upon contribution of the Dutch Belted pigmented coat. One of these chimeras was male (FIG. 2a), one female (FIG. 2b) and one probably a hermaphrodite. These results constitute the first proof of principle that chimeric rabbits can be generated by blastocyst injection of ES cell lines maintained in culture and extensively (15 to 22 times) passaged. In retrospect chimerism appeared to be attributable to the three dimensionally growing alkaline phosphatase positive ES cells, as further detailed below.

Indeed, the frequency of chimera formation following injection of ES cells into the blastocoel cavity was low—only 4% of live born animals. This might have been due to several factors, including 1) infrequent incorporation of ES cells into the developing embryo due to the prominent void space in the mature blastocyst into which the ES cells were introduced, 2) an inherent incompatibility of Dutch Belted ES cell lines with New Zealand White blastocysts, or 3) loss of pluripotency of the cell lines. Attempt to increase the frequency of delivery of ES cells to the developing inner cell mass by introducing the ES cells directly onto or into the developing inner cell mass, a prerequisite for incorporation into the subsequent embryo, did not result in a higher frequency or chimera formation. The use of Dutch White blastocysts (originating from the Dutch Belted strain by a natural point mutation) as recipients for ES cell injections also did not generate chimeras, thus eliminating the involvement of a strain barrier.

Additional experiments revealed that the absence of chimera formation with ES cells maintained in culture as described by Graves and Moreadith (1993) and the low efficiency with ES cells cultured as described in Example 1, starting from early passage GM3 cells was most likely due to the absence in the former and the low percentage in the latter of residual pluripotent ES cells. This was revealed by staining for alkaline phosphatase, which is present in undifferentiated cells, but rapidly lost upon differentiation (Benham et al., 1981). The occurrence of alkaline phosphatase positive cells in the original cell line was less than 1% after passage 10 (FIG. 1), although this frequency could be maintained under the improved culture conditions described herein. It appears that the flat epithelioid cell type (FIG. 1) originally thought to represent putative ES cells (Graves and Moreadith, 1993) are mostly alkaline phosphatase negative, unable to incorporate in the inner cell mass of the recipient blastocyst, and unable to generate chimeric offspring. Therefore new ES cell lines were derived as described in Example 3.

EXAMPLE 3

Improved Derivation of ES Cells

Improved methods for derivation of ES cells were developed which, in combination with the improved cell culture conditions, allowed the generation of five rabbit ES cell lines which consist of more than 80% undifferentiated alkaline phosphatase positive cells after 8 to 10 passages, as described below.

Superovulated Dutch Belted does were mated with Dutch Belted bucks. The blastocysts were flushed from the uterine horns on day 5.5 (postcoitus instead of 4 or 5 days postcoitus) and rinsed with Dulbecco's phosphate buffered saline supplemented with 3% bovine serum albumin (Cohn fraction V) plus 5% (v/v) antibiotic/antimycotic solution. The blastocysts were kept in rabbit ES medium (described above) at 39° C. in a 5% $CO_2$ incubator until further manipulation. The mucin coat and zona pellucida of the blastocysts were removed using acidified phosphate buffered saline (pH=2.5) and 0.5% pronase in phosphate buffered saline. The inner cell mass was prepared manually out of the surrounding trophectoderm cells with 2 needles and placed individually in a 96 well culture dish (plated with 12.5 days old, passage 1 mouse embryonic fibroblasts with a density equivalent to 3 to 4×10 cells per 10 cm dish).

The explanted inner cell masses were refed daily with the improved rabbit ES cell medium described above. After 2 days, the inner cell mass outgrowth was easily freed from remaining trophectoderm cells by gently lifting the trophectoderm outgrowth with a beveled glass pipet off the underlying feeder layer and by aspirating it into the glass pipet.

Only ES-like colonies, characterised by three dimensional growth were subsequently passaged onto new culture dishes. Therefor the 96 well was selectively trypsinized after 4 to 5 days with the trypsinization medium described above, thus allowing the selective passaging of ES cells and not of trophectoderm cells or mouse embryonic fibroblasts. The three dimensional growth typical of the improved rabbit ES cells has not been noticed before and is apparently a novel characteristic of such cell lines. Only with the improved culture conditions and the use of 5.5 days old embryos, could three dimensional undifferentiated ES cell colonies be maintained at high frequency in culture. The ES cells were passaged very gradually onto larger culture dishes at 4 to 5 days intervals, to maintain the ES cells at a very high density, another prerequisite to prevent differentiation and loss of pluripotency. The feeder densities on the subsequent culture dishes was maintained at densities equivalent of 3 to 4×10 cells per 10 cm dish.

The rabbit ES cell lines obtained by this procedure (FIG. 3) are more similar to pluripotent murine ES cell lines than any of the rabbit ES variants previously reported. The main characteristics are colony growth in three dimensions, high refractility and a small nuclear/cytoplasmic ratio. The most important characteristics are that after 10 passages, 80 to 90% of the ES cells remain undifferentiated as indicated by their positive staining for alkaline phosphatase (FIG. 3b), and negative staining for human cytokeratin 18 and mouse vimentin, which are known markers of differentiation (Viebahn et al., 1988; Piedrahita et al., 1990). These properties stand in major contrast with those of the earlier putative ES cell line (FIG. 1), where less than 1% of the cells were undifferentiated as judged by alkaline phosphatase positive staining. This enormous increase in the percentage of undifferentiated cells (from 1% to 80–90%) in frequently passaged rabbit ES cells, should markedly increase the efficiency of chimeric rabbit generation by ES cell injection into blastocysts and allow the generation of chimeric rabbits containing targeted genetic alterations.

REFERENCES

Babinet C, Bordenave G R (1980); Chimeric rabbits from immunosurgically-prepared inner cell mass transplantation. J Embryol Exp Morphoi 60:429–440.

Benham F J, Andrews F W, Knowles B B, Bronson D L, Harris H (1981): Alkaline phosphatase isozymes as possible markers of differentiation in human testicular teratocarcinoma cell lines. Dev. Bio 88:279–287.

Bongso A, Fong C-Y, Ng S-C, Ratman S (1994): Isolation and culture of inner cell-mass from human blastocysts. Hum Reprod 9:2110–2117.

Bradley A (1987): Production and analysis of chimeric mice. In: Teratocarcinomas and Embryonic Stem Cells: A Practical Approach (Ed. Robertson E J), IRI Press Ltd., Oxford, 1987, pp. 113–151.

Capecchi M R (1989): Altering the genome by homologous recombination. Science 244:1288–1292.

Doetschman T, Williams P, Maeda N (1988): Establishment of hamster blastocyst-derived embryonic stem (ES) cells. Dev Biol 127:224–227.

Du F, Giles J R, Foote R H, Graves K G, Yang X, Moreadith R W (1995): Nuclear transfer of putative rabbit embryonic stem cells leads to normal blastocyst development. J Reprod Fert 104:219–223.

Evans M J, Notarianni E, Laurie S, Moor R M (1990): Derivation and preliminary characterization of pluripotent cell lines from porcine and bovine blastocysts. Theriogenology 33:125–128.

Gardner R L, Munro A J (1974): Successful construction of chimeric rabbit. Nature 250:146.

Graves K H, Moreadith R W (1993): Derivation and characterization of putative pluripotential embryonic stem cells from preimplantation rabbit embryos. Mol Reprod Dev 36:424–433.

Iannaccone P M, Taborn G U, Garton R L, Caplice M D, Brenin D R (1994): Pluripotent embryonic stem cells from the rat capable of producing chimeras. Dev Biol 163:288–292.

Johnson L V, Calarco P G, Siebert L S (1977): Alkaline phosphatase activity in the preimplantation mouse embryo. J Embryol exp Morph 40:83–89.

Moustafa L (1974): Chimeric rabbits from embryonic cell transplantation. Proc Soc Exp Biol 147:485–488.

Nagy, A, J Rossant, R Nagy, W Abromow-Newerly, and Roder J C (1993): Derivation of completely cell culture derived mice from early-passage embryonic stem cells Proc Natl Acad Sci USA 90:8424–8428.

Nieman H, Strelchenko N (1994): Isolation of rabbit embryonic stem (ES) cell like cells. Theriogenology 41:265.

Notarianni E, Galli C, Laurie S, Moor R M, Evans M J (1991): Derivation of pluripotent, embryonic cell lines from the pig and sheep. J Reprod Fert Suppl 43:255–260.

Notarianni E, Laurie S, Moor R M, Evans M G (1990): Maintenance and differentiation in culture of pluripotential embryonic cell lines from pig blastocysts. J Reprod Fert 40:51–56.

Piedrahita J A, Anderson G B, BonDurant R H (1990): On the isolation of embryonic stem cells: Comparative behaviour of murine, porcine and ovine embryos. Theriogenology 34:879–891.

Robertson E J (1987): Embryo-derived stem cell lines; In/Teratocarcinomas and Embryonic Stem Cells: A Practical Approach (Ed. Robertson E J), IRI Press Ltd., Oxford, 1987, pp. 71–112.

Rubin E M, Barsh G S (1996): Biological insights through genomics: mouse to man. J Clin Invest 97:275–280.

Saito S, Strelchenko N, Nieman H (1992): Bovine embryonic stem cell-like cell lines cultured over several passages. Roux Arch Dev Biol 201:134–141.

Strojeck M, Reed M A, Hoover J L, Wagner T E (1990): A method for cultivating morphologically undifferentiated embryonic stem cells from porcine blastocysts. Theriogenology 33:901–913.

Sukoyan M A, Golubitsa A N, Zhelezova A I, Shilov A G, Vatolin S Y, Maximovsky L P, Andreeva L E, Mc Whir J, Pack S D, Bayborodin S I, Kerkis A Y, Kizilova H I, Serov O L (1992): Isolation and cultivation of blastocyst-derived stem cell lines from American mink. Mol Reprod Dev 33:418–431.

Talbot N C, Caird E R jr, Vernon G P, Powell A M, Nel N D (1993): Culturing the pig epiblast cells of the pig blastocysts. In Vitro Cell Dev Biol 29A:546–554.

Thomson J A, Kalishman J, Golos T G, During M, Harris C P, Becker R A, Hearn J P (1995): Isolation of a primate embryonic stem cell line. Proc Natl Acad Sci USA 92:7844–7848.

Viebahn C, Lane B E, and Ramackers F C S (1988) Keratin and Vimentin expression in early embryogenesis of the rabbit embryo. Cell Tissue Research 253:553–562.

Wilson J M (1996): Animal models of human disease for gene therapy. J Clin Invest 97:1138–1141.

Yang X, Foote R H (1988): Production of chimeric rabbits from morulae by a simple procedure. Gamete Res 21:345–351.

What is claimed is:

1. Pluripotent rabbit cell line, comprising at least 70% undifferentiated, pluripotent cells obtainable by isolating an inner cell mass of a 5.5 day postcoitus blastocyst and culturing the inner cell mass cells on feeder cells in rabbit ES medium, wherein the rabbit ES medium comprises high glucose Dulbecco's Modified Eagle Medium, 4 mM L-glutamine, 0.1 mM 2-mercaptoethanol, 148 units/ml penicillin G sodium, 148 microgram/ml streptomycin sulfate, 4 microgram/ml bovine insulin, $10^3$ units/ml murine Leukemia Inhibitory Factor, 20% fetal bovine serum and 1.5% MEM non-essential amino acid solution, wherin the fedder cells are 12.5 days old Mouse Embryonic Feeder cells in a density of 3 to $4 \times 10^6$ cells per 10 cm petri dish, and wherein the inner cell mass cells are cultured over various passages and the inner cell mass cells are trypsinized before each passage with a selective trypsinization medium consisting of 0.1% collagenase, 1% chicken serum and 0.03% trypsin-ETDA in phosphate buffered saline, such that a pluripotent rabbit cell line results.

2. A method for producing a pluripotent rabbit cell line, comprising about 70% undifferentiated pluripotent cells comprising the steps of:

a) isolating an inner cell mass of a 5.5 day postcoitus blastocyst, and b) culturing innner cell mass cells on feeder cells in rabbit ES medium, wherein the rabbit ES medium comprises high glucose Dulbecco's Modifed Eagle Medium, 4 mMglutamine, 0.1 mM 2-mercaptoethanol, 148 units/ml penicillin G sodium, 148 microgram/ml streptomycin sulfate, 4 microgram/ml bovine insulin, $10^3$ units/ml murine Leukemia Inhibitory Factor, 20% fetal bovine serum and 1.5% MEM non-essential amino acid solution, wherein the feeder cells are 12.5 days old Mouse Embryonic Feeder cells in a density of 3 to $4 \times 10^6$ cells per 10 cm petri dish, and wherein the inner cell mass cells are cultured over various passages and the inner cell mass are trypsinized before each passage with a selective trypsinization medium consisting of 0.1% collagenase, 1% chicken serum and 0.03% trypsin-EDTA in phosphate buffered saline, such that a pluripotent rabbit cell line results.

3. Selective trypsinization medium, consisting of 0.1% collagenase, 1% chicken serum and 0.03% trypsin-EDTA in phosphate buffered saline.

* * * * *

UNITED STATES PATENT AND TRADEMARK OFFICE
CERTIFICATE OF CORRECTION

PATENT NO. : 6,103,523
DATED : August 15, 2000
INVENTOR(S) : Randall MOREADITH et al.

It is certified that error appears in the above-identified patent and that said Letters Patent is hereby corrected as shown below:

Claim 1 Column 9 Line 9 "fedder" should read --feeder--.

Claim 2 Column 10 Line 4 "mMglutamine" should read --mM L-glutamine--.

Claim 2 Column 10 Line 14 after "mass" insert --cells--.

Signed and Sealed this

Twenty-fourth Day of April, 2001

NICHOLAS P. GODICI

Attest:

Attesting Officer

Acting Director of the United States Patent and Trademark Office